US008765378B2

(12) United States Patent
Gronowitz

(10) Patent No.: US 8,765,378 B2
(45) Date of Patent: Jul. 1, 2014

(54) METHOD AND KIT FOR DETERMINATION OF THYMIDINE KINASE ACTIVITY AND USE THEREOF

(75) Inventor: J. Simon Gronowitz, Uppsala (SE)

(73) Assignee: Biovica International AB, Uppsala (SE)

( * ) Notice: Subject to any disclaimer, the term of this patent is extended or adjusted under 35 U.S.C. 154(b) by 236 days.

(21) Appl. No.: 11/883,187

(22) PCT Filed: Feb. 24, 2006

(86) PCT No.: PCT/SE2006/000246
§ 371 (c)(1),
(2), (4) Date: Jul. 27, 2007

(87) PCT Pub. No.: WO2006/091158
PCT Pub. Date: Aug. 31, 2006

(65) Prior Publication Data
US 2008/0248472 A1    Oct. 9, 2008

(30) Foreign Application Priority Data

Feb. 25, 2005 (SE) ...................................... 0500432

(51) Int. Cl.
*C12Q 1/68* (2006.01)
(52) U.S. Cl.
USPC ....... 435/6.12; 435/91.1; 435/91.2; 536/23.1; 536/24.33
(58) Field of Classification Search
USPC ........ 435/6, 91.1, 91.2, 6.12; 536/23.1, 24.33
See application file for complete search history.

(56) References Cited

U.S. PATENT DOCUMENTS

| 7,488,577 | B2 * | 2/2009 | Kallander et al. | 435/6 |
| 2006/0171977 | A1 * | 8/2006 | Nennstiel et al. | 424/405 |

FOREIGN PATENT DOCUMENTS

| EP | 0094923 A2 | 11/1983 |
| WO | 90/06373 A1 | 6/1990 |
| WO | WO 9006320 A1 | 6/1990 |
| WO | WO 2004011627 A2 | 2/2004 |
| WO | WO 2004/100760 A1 | 11/2004 |

OTHER PUBLICATIONS

Armstrong B et al, "Selective Inhibition of Thymidine Kinase Isoenzymes by (E) -5-(2-Bromovinyl)-2-Deoxyuridine", Biochemical Society Transactions, Colchester, Essex, GB, vol. 18, No. 2, 1990, p. 270, XP001070196, ISSN:0300-5127.
Ohrvik Anders et al, "Sensitive nonradiometric method for determining thymidine kinase I activity" Clinical Chemistry, vol. 50, No. 9, Sep. 2004 (Sep.2004), pp. 1597-1606, XP002470247, ISSN:0009-9147.
R.G. Wickremasinghe, et al., Gel Filtration of a Complex of DNA Polymerase and DNA Precursor-Synthesizing Enzymes from a Human Lymphoblastoid Cell Line, Gene Structure and Expression, Biochemica et Biophysica Acta, 1983, vol. 740, 243-248.
Q. He et al., "The Clinical Significance of thymidine kinase 1 measurements in serum of beast cancer patients using anti-TK1 antibody," The International Journal of Biological Markers, Apr.-Jun. 2000; vol. 15 No. 2, pp. 139-146.
First Examination Report dated Jan. 31, 2013, issued by the Government of India Patent Office in corresponding Application No. 6106/DELNP/2007.

* cited by examiner

*Primary Examiner* — Kenneth R. Horlick
*Assistant Examiner* — Joyce Tung
(74) *Attorney, Agent, or Firm* — Bacon & Thomas, PLLC

(57) ABSTRACT

A method and assay kit for determination of thymidine kinase (TK) activity in a biological sample, such as blood, serum, plasma, Cerebral Spinal Fluid (CSF), pleural fluid, ascites, tissues, cells and extracts thereof, is described. The method comprises contacting, in a buffer, a Basic Reaction Mixture comprising: solid surface-attached primer and/or template, a modified deoxy nucleoside, such as BromodeoxyUridine, IododeoxyUridine, Fluorodeoxy-Uridine or VinyldexoyThymidine as a kinase enzyme substrate, a phosphate donor, a nucleotide polymerizing enzyme, and a kinase enzyme source devoid of TK activity, such as a yeast extract, with the biological sample. After incubation the amount of modified deoxy nucleoside that has been incorporated into the solid surface-attached primer and/or template, is determined and the TK activity present in the biological sample is directly proportional to the amount of incorporated modified deoxy nucleoside. The method and assay kit are useful in the diagnosing, prognosis monitoring of disease progression and treatment effects of cell-proliferation disorders or diseases, such as cancer, and in the screening of compounds, e.g. new drug candidates, affecting enzymatic pathways, which may obstruct the formation of thymidine phosphates or interfere with nucleic acid synthesis.

22 Claims, 4 Drawing Sheets

METHOD AND KIT FOR DETERMINATION OF THYMIDINE KINASE ACTIVITY AND USE THEREOF

The present invention relates to a non-radioactive method and kit for determination of thymidine kinase (TK) activity in biological samples. The invention is useful in the diagnosing, monitoring and prognosis of cell-proliferation disorders or diseases, such as cancer and certain viral infections, and in screening of compounds, e.g. new drug candidates, affecting enzymatic pathways which may obstruct the formation of thymidine monophosphate and/or interfere with the nucleic acid synthesis after phosphorylation.

BACKGROUND

Before cell division, the DNA carrying the genetic information has to duplicate by a DNA-polymerase. This requires among other necessary components the presence of large amounts of substrates, i.e. the presence of all four deoxyribonuclotides, e.g. deoxy Thymidine Tri-Phosphate (TTP, FIG. 2C). TTP is synthesized de novo according to the pathway illustrated in FIG. 1. In addition, mammals and many other species encode the TK, which exclusively is expressed in G1-S cell cycle stage and salvages Thymidine (T, FIG. 2A) into the metabolism by phosphorylating it to Thymidine Mono-Phosphate (TMP, FIG. 2B) (FIG. 1) (1, review). Determination of incorporated radioactive T into the DNA of cells in culture has thus traditionally been used as a measure of the rate of cell division. TK activity in human plasma or serum from healthy individuals and patients affected with various tumour diseases was shown during the 1980-ies (2, 3). Absence of TK activity in the spinal fluid was found in healthy individuals, while various levels were found in patients with brain tumours (4). Since then TK analysis has become more common in clinical medicine, especially in connection with different blood malignancies (5-10).

There exist two cellular genes encoding TK, TK1 being the major form in cell division is released into the serum as s-TK. This is the form over-expressed in serum in tumour disease and is measured using most of the current assays including the assay according to the invention. The TK2 form exists purely in the mitochondrion. Besides being localized to the mitochondrion TK2 also has a different substrate spectrum and kinetic parameters than TK1 (1).

The radioactivity included in the procedure in the hitherto only commercially available laborious serum TK (s-TK) assay has hampered its spread and use in clinical medicine (2). Being directly correlated to the degree of tumour cell division in vivo, s-TK is a complement to many tumour markers that merely indicate the tumour presence by over-expression of foetal antigens or products specifically produced by the differentiated cell. For example, prostate specific antigen (PSA) is an early marker of excess amounts of prostate cells, and the elevations of the level of antigen are detected long before the TK activity elevation. However, when the tumour starts to de-differentiate and starts to grow faster, PSA antigen (Kallikrein 3) disappears while increased s-TK activity is found (11). Thus, in addition to its use for monitoring tumour cell replication in patients, with or without therapy, the s-TK activity and alteration in its kinetics also singles out a patient with regard to a need for change in therapeutic treatment. The importance of a given s-TK level for the patient's outcome varies between different tumour types and relates naturally both to type of therapy installed, age of patient and other factors which make s-TK an important marker to include in multivariate models for use in clinical medicine (12).

As mentioned, in the prior art, the TK has either been detected by its activity or by procedures detecting the physical presence of the TK1 protein (24 kd gene expressed size) (13). The latter procedures pick up both active and inactive enzyme. Thus, these protein-detection assays correlate poorly to s-TK activity. This is not an unexpected phenomenon as TK1 is only active in the G1 to S stages of the cell cycle, i.e. at cell division, while the TK1 protein, or degradation products thereof, might have a different half-life. Thus, only the state of art measuring TK activity will be addressed here.

In general, all TK activity assays consist of an incubation of the sample to be analyzed with T or an analogue thereof, in presence of a phosphate donor (e.g. Adenosine Tri-Phosphate, ATP) and $Mg^{2+}$ (or $Mn^{2+}$). Thereafter the amount of product, i.e. TMP or any T-analogue monophosphate is determined as follows:

A) In the early described TK activity assays, $^3$H-labelled thymidine (T) was used as substrate. TMP was bound to Di-Ethyl Amino Ethyl (DEAE)-charged filter paper, which was subsequently washed in order to remove unused T substrate. After drying the filter paper the $^3$H radioactivity was measured in a beta-counter. However, still radioactive tests are developed which indicate the persistent interest in using s-TK as a marker for cellproliferation (14).

B) In the commercially available Prolifigene® TK-REA (DiaSorin S.p.A. Saluggia, Italy) assay, radioactive Iodo-deoxy Uridine ($^{125}$IdU) is used as substrate for TK. The Mono-Phosphorylated product; Iodo-deoxy Uridine Mono-Phosphate ($^{125}$IdUMP), is separated by binding it to self-sedimenting Aluminium Hydroxide ($Al(OH)_3$) which is subsequently washed in order to remove unused $^{125}$IdU. The $^{125}$I radioactivity bound to the $Al(OH)_3$ powder is subsequently counted in a gamma-counter (2, 3).

C) The recently published non-radioactive TK assays (15, 16) disclose a similar technology to quantify TK1 activity. In these assays either Azido-Thymidine (AZT, FIG. 2D) or Bromo-deoxy Uridine (BrdU, FIG. 2A) was used as substrate, and the respectively formed Monophosphate (AZTMP or BrdUMP FIG. 2B) was quantified by analyzing the capacity of the reaction solution to compete with the binding of enzyme-labelled AZTMP or BrdUMP to an anti-AZTMP or anti-BrdUMP antibody immobilized on the bottom of wells in a second 96 well microtiter plate. (i.e. detection by competitive ELISA).

Albeit avoiding radioactivity, the hitherto known non-radioactive assay does not seem efficient enough for analyzing biological samples containing low levels of TK, since it measures the reduction of a bound tracer, which requires rather high amounts of TK product to be present in the analyzed sample (15, 16). This hampers good resolution of the TK activity in the normal range, which can differ more than three fold between young and old individuals, and particularly when the TK assay is used on biological samples devoid of measurable reference levels, such as spinal, pleural, ascites and other body fluids.

Recently a new recombinant host cell line was disclosed utilizing the complementing activity of TMPK, NdK alone or in combination with TK wherein the TMPK, NdK or the TK gene was deleted. That invention is directed to creating a recombinant cell line and kit including the cell line for screening of compounds affecting kinase pathways (17).

DESCRIPTION OF THE INVENTION

The present invention provides a sensitive non-radiometric thymidine kinase assay that can be easily automated, if desired. The TK product is directly processed to be immobilized on a solid surface and the TK activity level is directly quantified e.g. using ELISA procedure (18) without transfer of samples for secondary measurements.

The new method quantifies the thymidine kinase (TK) (ATP: thymidine-5'-phopsphotransferase: E.C. 2.7.1.21) activity in a biological sample, e.g. a body fluid sample. The method enables simple, inexpensive, accurate and highly sensitive determination of TK activity in a biological sample, e.g. body fluid or a tissue or cell sample, as well as pure recombinant TK isozymes.

Thus, the invention is directed to a method for determination of thymidine kinase (TK) activity in a biological sample comprising the steps of contacting, in a container containing a single stranded polynucleotide as a primer or template attached to a solid surface, a Basic Reaction Mixture, in a buffer, comprising the following components: a non-attached single stranded polynucleotide as a template and/or primer, a modified deoxy nucleoside as a kinase enzyme substrate, a phosphate donor, a nucleotide polymerizing enzyme, and a kinase enzyme source devoid of TK activity, with the biological sample, incubating the mixture, optionally washing the incubated mixture to remove non-attached reaction components, determining the amount of the modified deoxy nucleoside that has been incorporated into the solid surface-attached primer and/or template, and determining the TK activity present in the biological sample from the amount of incorporated modified deoxy nucleoside The expression "devoid of TK activity" is in the present specification and appended claims intended to mean that there is so low amount of TK activity, if at all, present that it will not interfere with the performance of the method of the invention.

Further, it should be understood that the determined TK activity is proportional to the amount of incorporated modified nucleoside.

In a presently preferred embodiment the incubated mixture is washed and the determination of the amount of incorporated modified deoxy nucleoside is made by adding to the incubated mixture a labeled affinity molecule with affinity for the modified deoxy nucleoside and determining the amount of modified deoxy nucleoside that has been incorporated by determining the amount of attached labeled affinity molecule with the aid of the label.

In an embodiment of the method of the invention the kinase enzyme source is selected from the group consisting of a mammalian cell line extract devoid of TK activity, a fungal cell line extract devoid of TK activity, a bacterial cell line extract devoid of TK activity, a combination of TMPK and Nucleoside di-phosphate kinases (NdK) from purified mammalian cell extracts, a combination of TMPK and NdK from purified fungal cell extracts, a combination of TMPK and NdK from purified bacterial cell extracts, a combination of recombinant mammalian TMPK and recombinant mammalian NdK, a combination of recombinant fungal TMPK and recombinant fungal NdK, and a combination of recombinant bacterial TMPK and recombinant bacterial NdK. It should be understood that the kinases might come from different sources in the above combinations. Preferably, the enzyme source is a yeast cell extract, such as an extract of *Saccharomyces cerevisiae*.

In another embodiment the incorporated modified nucleoside is derived from a correspondingly modified deoxy nucleoside.

In yet another embodiment, the modified deoxy nucleoside kinase enzyme substrate is selected from the group consisting of BromodeoxyUridine, IododeoxyUridine, FluorodeoxyUridine and VinyldexoyThymidine, and it is preferably BromodeoxyUridine.

In a preferred embodiment the solid surface is a plastic surface, e.g. a plastic microtiter plate. However, the solid surface may be of another material onto which affinity molecules can be attached, such as plastic beads, magnetic beads, and agarose or silica surfaces as chips or beads.

In still another embodiment the solid surface-attached single stranded polynucleotide is attached via its 5'-end or immobilized using imidazole in activated plates.

Preferably the biological sample analyzed by the method of the invention is selected from the group consisting of blood, serum, plasma, Cerebral Spinal Fluid (CSF) (4), pleural fluid, ascites, tissues, cells and extracts thereof. Tissue and cell samples refer to cytosolic or nuclear extract samples.

The invention is also directed to an assay kit for determination of thymidine kinase (TK) activity in a biological sample comprising, in several separate containers, a solid surface-attached single stranded polynucleotide as a primer and/or template, a non-attached single stranded polynucleotide as a template and/or primer, a modified deoxy nucleoside as a kinase enzyme substrate, a phosphate donor, a nucleotide polymerizing enzyme, and a kinase enzyme source devoid of thymidine kinase (TK) and a buffer.

In a preferred embodiment of the assay kit of the invention, the kit comprises reference TK for standardization of the assay. Examples of a suitable reference are serum from a mammal having a tumour disease, and growing cells suspended in animal serum.

In a further preferred embodiment of the assay kit of the invention, the kit additionally comprises one or several microtiter plates containing in one or several wells surface-attached single stranded polynucleotide (18).

In another embodiment of the kit of the invention, the assay kit additionally comprises a labelled affinity molecule with affinity for a modified deoxy nucleoside, preferably an enzyme labelled affinity-conjugate, such as an antibody labelled with alkaline phosphatase or with horseradish peroxidase.

Also in an embodiment of assay kit of the invention the kinase enzyme source is selected from the group consisting of a mammalian cell line extract devoid of TK activity, a fungal cell line extract devoid of TK activity, a bacterial cell line extract devoid of TK activity, a combination of thymidylate kinase (TMPK) and Nucleoside di-phosphate kinases (NdK) from purified mammalian cell extracts, a combination of TMPK and NdK from purified fungal cell extracts, a combination of TMPK and NdK from purified bacterial cell extracts, a combination of recombinant mammalian TMPK and recombinant mammalian NdK, a combination of recombinant fungal TMPK and recombinant fungal NdK, and a combination of recombinant bacterial TMPK and recombinant bacterial NdK. It should be understood that the kinases might come from different sources in the above combinations. Preferably, the enzyme source is a yeast cell extract, such as an extract of *Saccharomyces cerevisiae*.

The invention is further directed to the use of the method and/or the assay kit of the invention in the diagnosing, monitoring and/or prognosis of cell-proliferation disorders or diseases, such as cancer or certain viral infections, in mammals, especially humans.

The invention is additionally directed to the use of the method and/or the assay kit of the invention in the screening of compounds, e.g. new drug candidates, affecting enzymatic pathways, which may obstruct the formation of thymidine phosphates.

The two last mentioned aspects of the invention may be formulated in an alternative way, namely as a method for use in the diagnosing, monitoring and prognosis of cell-proliferation disorders or diseases, such as cancer or certain viral infections, in mammals, especially humans, comprising the method according to the invention and/or the assay kit according to the invention, and a method for use in the screening of compounds, e.g. new drug candidates, affecting enzymatic pathways which may obstruct the formation of thymidine phosphates or interfere with the synthesis of nucleic acids comprising the method according to the invention and/or the assay kit according to the invention.

An important feature of the method of the invention is that the determination of TK activity in a body fluid sample is achieved by utilising a cell extract devoid of TK activity. This in combination with a preferred solid phase immunodetection of BrdUMP incorporation overcomes both the problem connected with the current radioactive method (Prolifigen® TK-REA, DiaSorin S.p.a. Saluggia, Italy) (2, 3) and with the non-radioactive methods described (15, 16). Not only does the present invention provide a non-radioactive method and kit for the detection of serum TK activity, the method is also simple to perform, robust and provides an analytically useful method for diagnostic purposes.

For the phosphorylation steps to occur in the method of the invention there is an absolute requirement for a phosphate donor to be present in the Basic Reaction Mixture in a buffer. As phosphate donors several nucleotide tri-phosphates can be used, especially ATP. Preferably the choice is a nucleotide that will not become incorporated into the growing chain of the primer/template system on the solid surface. It is particularly preferred to use a ribo-tri-phosphate nucleotide as phosphate donor.

In one embodiment of the invention there is provided a method for the determination of TK activity in a biological sample by contacting, in a buffer, the sample with a Basic Reaction Mixture, containing a single stranded polynucleotide attached to a solid surface as a template and/or primer, a non-attached single stranded polynucleotide as a template and/or primer, and a cell extract devoid of TK activity so that the biological sample provides the only source for the TK. The TK activity in the biological sample is then determined by determination of the amount of modified nucleoside that has been incorporated by polymerase(s) into the newly synthesized double stranded nucleic acid attached to the solid surface, e.g. polymerase-directed solid phase incorporation of BrdUMP that is subsequently detected by using an enzyme-antibody conjugate against incorporated BrdU.

In a preferred embodiment the extract, devoid of TK activity, is derived from an extract of eukaryotic cells. In an even more preferred embodiment the extract is derived from extracts of mammalian cells. In a further preferred embodiment the extract, devoid of TK activity, is derived from purified mammalian cell extract e.g. using, but not limited to, affinity purification. In another preferred embodiment the extract, devoid of TK activity is constructed by combining the recombinant enzymes TMPK (Thymidylate kinase; EC 2.7.4.9; ATP:dTMP phosphotransferase) and NdK (EC 2.7.4.6; Nucleoside diphosphate (NDP) kinases) from recombinant cells, exemplified but not limited to, cloned yeast TMPK and NdK genes expressed in a suitable bacterial host strain such as *Escherichia coli*. In yet another preferred embodiment the extract is derived from a fungus. In a particularly preferred embodiment the cell extract, devoid of TK activity, is derived from baker's yeast, *Saccharomyces cerevisiae*.

The present invention reveals that TK activity, which is present in a biological sample, can be detected and determined by using a cell extract devoid of TK activity as a kinase enzyme source combined with a polymerase directed incorporation of a modified nucleoside.

The determination of the amount of incorporated modified nucleoside can be made in a number of different ways, such as by detection of the modification of the nucleoside, e.g. Br in BrdUMP. The invention is illustrated by use of an immunological method, namely Enzyme Linked Immuno Sorbent Assay (ELISA).

Thus, an enzyme-labeled affinity conjugate is used for the determination of the incorporated modified nucleoside, which is related to the level of cell proliferation in the biological sample. Examples of affinity molecules include antibodies, such as monoclonal antibodies or antigen-binding fragments thereof.

The present invention is illustrated by use of the presently preferred modified nucleoside, BrdU, and an antibody directed against BrdU, but several other modified nucleosides are known in the art, which can become phosphorylated by the TK and thus can be used in the method of the present invention. These include, but are not limited to; VinyldexoyThymidine, FdU and IdU (FIG. 2A). In fact the two last mentioned modified nucleosides have been used in the method of the invention and gives results comparable to BrdU although they require longer incubation times, probably due to the lack of an ideal monoclonal antibody since the available anti-BrdU antibody conjugate was used also in these experiments.

In a preferred embodiment the polymerase, used for the incorporation of BrdUMP into the solid surface primer template setup, is RNA directed DNA polymerase (RNA template dependant DNA polymerase=Reverse Transcriptase) (RT) and the solid surface attached nucleic acid template is poly-rA (polyriboadenylic acid). In another equally preferred embodiment the polymerase is a DNA directed DNA polymerase and the solid surface attached nucleic acid template is an oligo-dA and the primer is a shorter oligo-dT complementary to the primer. In a further embodiment the polymerase is any polymerase known in prior art and the solid phase attached template is a variable DNA with and without a homopolymeric region, and the shorter primer is complimentary either to a variable region or the homopolymeric part of the template. Depending on how the nucleic acid is attached to the surface, either the template or primer is attached to the surface. A provision is that there cannot be two ribo-nucleic acid strands forming the initial primer/template system.

A number of native and modified DNA directed DNA polymerases are known in the art; these are exemplified by, but not limited to, eukaryotic DNA polymerase alpha from various sources, *Escherichia coli* DNA polymerase I, modified Klenow fragment from *Escherichia coli* DNA polymerase I, Phage T4 polymerase native or modified, Taq polymerase from *Thermophilus aquaticus* native or modified, Vent polymerase from *Thermococcus litoralis* and Pfu polymerase from *Pneumococcus furiousus*.

Several native and modified RNA-directed DNA-polymerases, (Reverse Transcriptase=RT) (EC: 2.7.7.49) are known in the art; these are exemplified by, but not limited to, alfalfa Mosaic Virus RT AMV-RT), Moloney Murine Leukemia Virus RT (M-MuLV-RT), Simian Immunodeficiency Virus (SIV RT) and Human Immunodeficiency Virus (HIV), which are typical examples of this type of polymerases.

The length of the template is preferably 30 to 300 nucleotides long and the primer is preferably 10 to 30 nucleotides long. Methods for covalently attaching proteins to the solid surface of polystyrene plastic 96-well microwell plates are well known in the art. Binding to the polystyrene surface can be facilitated by the use of Imidazole, which is hereby included as an example, but not limiting, of this technology. Use of 1-ethyl-3-(3-dimethylaminopropyl)carbodiimide (EDCC) activated surface to couple 5'-amine modified oligonucleotide primers is well known in the art using photo coupling.

Many different methods for employing technologies for the measurement of bio-molecules present in a sample, using Enzyme Linked Immuno Sorbent Assay (ELISA) technology are well known in the art. In a preferred embodiment a monoclonal antibody directed against the hapten BrdU, is conjugated to the enzyme Alkaline Phosphatase, (AP) (Alkaline Phosphatase: Orthophosphoric-monoester phosphohydrolase (alkaline optimum), EC 3.1.3.1.). However, any other enzyme known in the prior art to be useful for ELISA procedure can be used in the present invention, such as an enzyme conjugated to the anti-BrdU antibody, e.g. horseradish peroxidase. (Hydrogen peroxide oxidoreductase EC 1.11.1.7) (HRP). In another approach, any chromatophore, fluorophore, luminophore that is known to the prior art may be conjugated to the tracer antibody, e.g. the anti-BrdU antibody.

Several suitable substrates for either AP or HRP are well known in the art. Cleavage of the substrate para-Nitro Phenyl Phosphate (pNPP) by the AP turns the substrate colour from colourless to yellow. The absorbance can be read at 405 nm wavelength using a spectrophotometer. Chemiluminescent AP substrates include, but are not limited to, derivatives of adamantyl 1,2-dioxethane (e.g. AMPPD, CSPD, CDP, and CDP-Star substrates all marketed by Tropix (Bedford, Mass., US)), which emit a steady state glowing light at 477 nm upon de-phosphorylation by AP and the subsequent decomposition of the remaining molecule. An example of, but not a limitation to, fluorescent substrates for AP is 4-Methyl Umbelliferyl Phosphate (4-MUP). After dephosphorylation of MUP, the remaining Methyl Umbelliferyl (MU) is excited at 370 nm wavelength. The emitted fluorescence is detected at 430 nm using a fluorometer.

DESCRIPTION OF THE DRAWINGS

Figures for the TK activity solid surface ELISA assay.

A. Nucleosides

| R-Substitution | Compound |
|---|---|
| CH$_3$ | Thymidine |
| I | Iodo-deoxyUridine |
| Br | BromodeoxyUridine |
| F | Fluoro-deoxyUridine |
| H | deoxyUridine |

B. Nucleotide Mono-Phosphates

| R-Substitution | Compound |
|---|---|
| CH$_3$ | TMP |
| I | IdUMP |
| Br | BrdUMP |
| F | FdUMP |
| H | dUMP |

C. Nucleotide Tri-Phosphates

| R-Substitution | Compound |
|---|---|
| CH$_3$ | TTP |
| I | IdUTP |
| Br | BrdUTP |
| F | FdUTP |
| H | dUTP |

D. Azidothymidine

| 3'-Substitution | Compound |
|---|---|
| N$_3$ | AZT |

Figure 1:
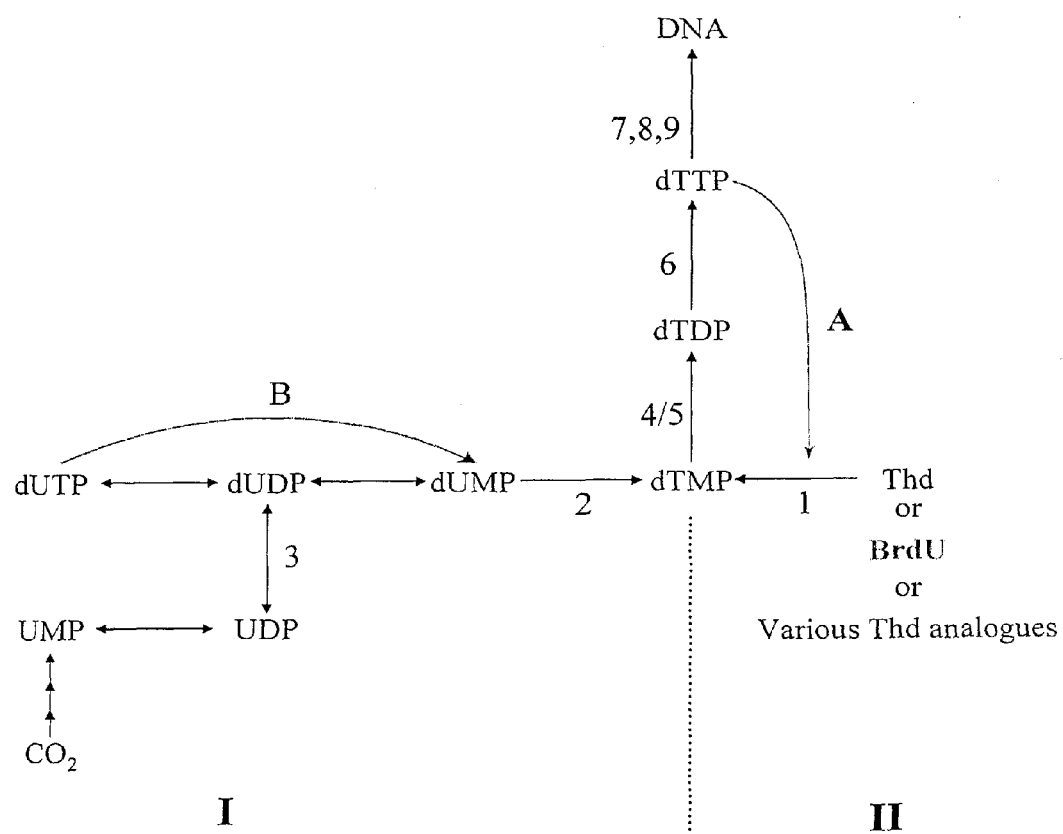
FIG. 1. Different pathways of TTP production in the mammalian cell.
Pathways: I. de Novo pathway, II. salvage pathway.
Relevant Enzymes: 1. Thymidine kinase (TK), 2. Thymidylate synthase (TS), 3. ribonucleotide reductase (RR), 4. Thymidylate kinase(dTMPK), 5 deoxy ribonucleoside monophosphate kinase (dNMPK), 6. nucleoside diphosphate kinase (NDPK), 7. Terminal Transferase (TT), 8. RNA-dependent DNA polymerase (RT), 9. DNA dependent DNA Polymerase (DNA Pol)
Important regulating factors: A. feedback inhibition, B. dephosphorylation by the enzyme Deoxyuridine-triphosphatase (dUTPase)
Figure 2:
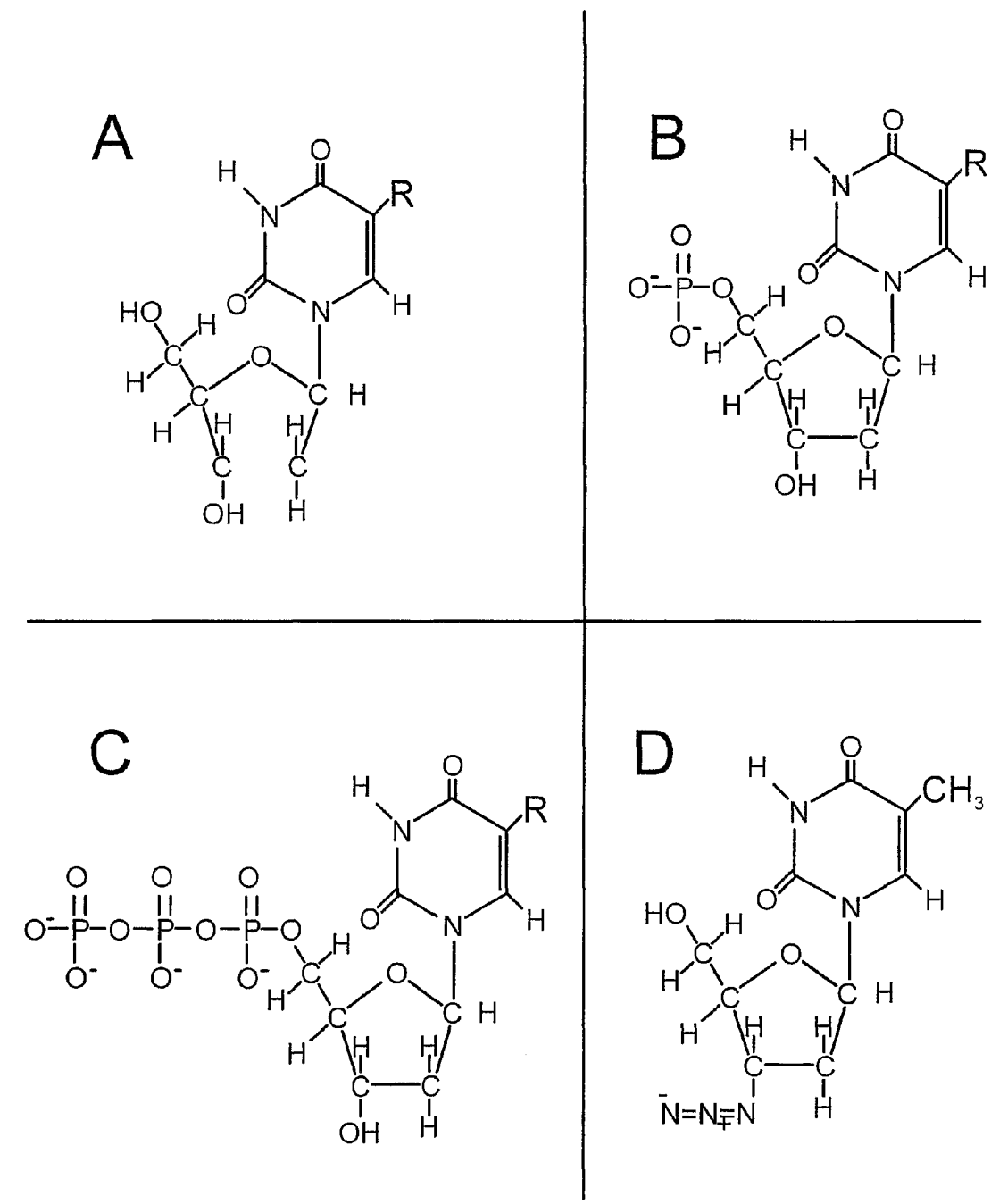
FIG. 2. Modification for thymidine nucleosides and nucleotide analogues
Figure 3:
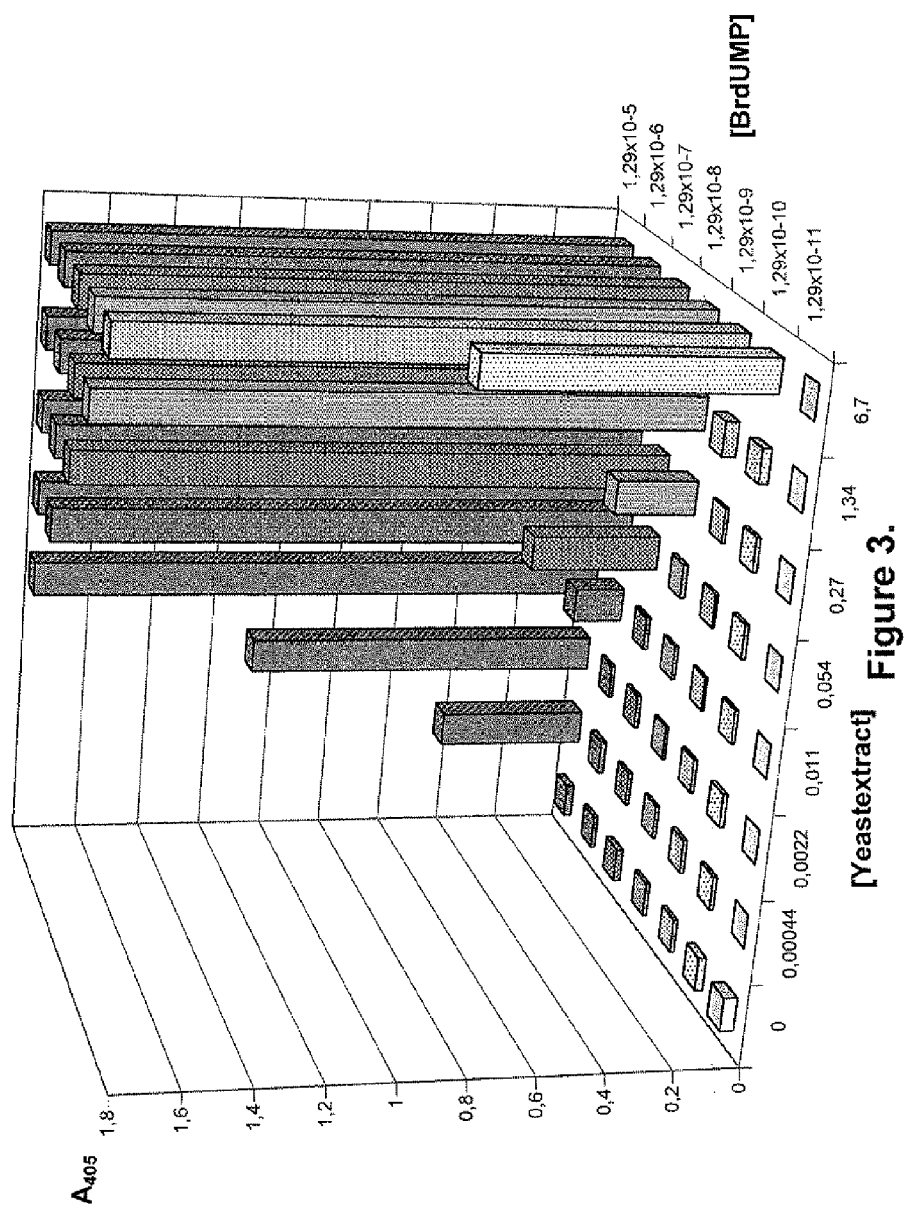

FIG. 3. Capacity of different yeast extract concentrations together with RT, to detect various BrdUMP concentrations.

Figure 4:
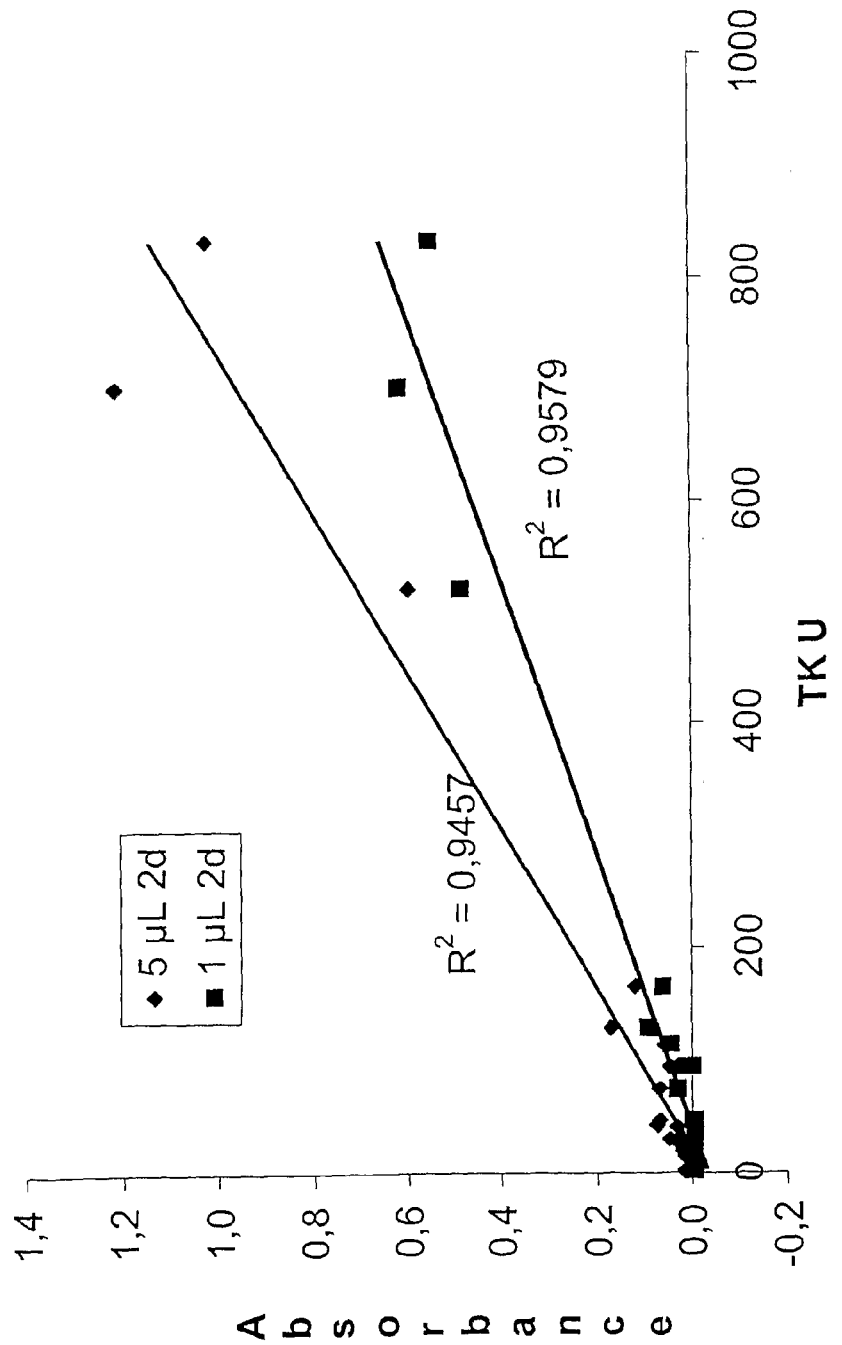

FIG. 4. S-TK measurement capacity of the assay according to the invention (A$_{405}$), using 2d extract incubation and two different amounts of each sera, 5 and 1 microliter, respectively, and correlation with the Prolifigen® TK-REA (TK U).

ABBREVIATIONS

4-MUP 4-Methyl Umbelliferyl Phosphate
Al(OH)$_3$ Aluminium Hydroxide
AMPPD Adamantyl 1,2-dioxetane aryl phosphate
AP Alkaline Phosphatase: EC 3.1.3.1; Orthophosphoric-monoester phosphohydrolase (alkaline optimum)
ATP Adenosine 5'-Tri-Phosphate
AZT 3'-azido-3'-deoxythymidine
BrdU BromodeoxyUridine
BrdUMP BromodeoxyUridine Mono-Phosphate
BrdUTP BromodeoxyUridine Tri-Phosphate
CSF Cerebral Spinal Fluid
DEAE Di-Ethyl Amino Ethyl
DTT Dithiothreitol
EDCC 1-ethyl-3-(3-dimethylaminopropyl)carbodiimide
EDTA Ethylenediamineteraacetic acid
EGTA Ethylene glycol-bis[beta-aminoethyl ether]-N,N,N'N'-tetraacetic acid
ELISA Enzyme Linked Immuno Sorbent Assay
FdU Fluorodeoxy Uridine
HIV Human Immunodeficiency Virus
HRP Hydrogen peroxide oxidoreductase EC 1.11.1.7
IdU Iododeoxy Uridine
NdK Nucleoside di-phosphate kinases: EC 2.7.4.6
pNPP para-Nitro Phenyl Phosphate PSA Prostate Specific Antigen
RT Reverse Transcriptase;RNA-directed DNA-polymerase: EC:2.7.7.49
SIV RT Simian immunodeficiency virus reverse trancriptase
TK Thymidine kinase: E.C. 2.7.1.21; ATP: thymidine-5'-phosphotransferase
TMPK Thymidylate kinase: EC 2.7.4.9; ATP:dTMP phosphotransferase
TMP deoxyThymidine Mono-Phosphate
TTP deoxyThymidine Tri-Phosphate
dUTP 2'-deoxyUridine 5'-Tri-Phosphate

EXAMPLE 1

Preparation of Kinase Extracts from the Yeast *Saccharomyces cerevisiae* which Complement TK Activity Yeast extract containing complementing/rescuing kinase activity was prepared in collaboration with the Uppsala Yeast Resource competence centre (www.yeastlab.vbiol.slu.se). Briefly;
Preparation of Yeast Cell Extracts.

200 mL of Gal-medium (1% yeast extract; Bacto™ Yeast Extract. DIFCO; 2% peptone, Bacto™ Peptone, BD; 2% galactose (Sigma) and 2% Agar (Bacto™ Agar; DIFCO) was inoculated with fresh *Saccharomyces cerevisiae* strain G116 (genotype: MATa ura3-52 his3 leu2::pLEU-lexAop6). Yeast cells were grown over night at 30° C. and allowed to reach a density of $OD_{600}$ nm of approximately 1.2. Cells were next harvested by centrifugation at 230×G for 5 min at 4° C., using four 50 mL Falcon™ polypropylene screw cap tubes. The pellets were each re-suspended and washed in 40 mL sterile ice-cold MilliQ™ water and again centrifuged at 230×G for 5 min at 4° C. MilliQ™ water was decanted off and discarded. Cells were next re-suspended in the remaining MilliQ™ Water by pipetting. Each yeast suspension in the 50 mL Falcon™ polypropylene screw cap tubes (approx. 0.8 g per 2.2 mL microtube, Sarstedt (Cat#: 72.694.006) was transferred to a 2.2 mL screw cap microtube, which was weighed before adding the yeast suspension, and centrifuged at 230×G for 2 min in a cold room (8° C.). Remaining water was poured off and discarded. Remaining pellets were weighed (approx. 0.4 g per 2.2 mL microtube). The weight was marked on the outside of the 2.2 mL microtube. Cells were subsequently stored at −80° C. prior to preparation of the complementing extracts.
Preparation of Complementing Yeast Extracts.

The yeast cell pellets were put at 25-28° C. until completely thawed (between 15 and 20 min) and were then kept in an ice bath prior to the yeast extract preparation procedure. All subsequent work was performed in a cold room facility (8° C.). To each 2.2 mL microtube containing 0.4 g yeast cell pellet was added approximately 0.5pellet volumes of 3× Breaking buffer, adjusted using the microtube volume surface indicator (1× Breaking buffer see Table 1). Next 1 mL of Zirkonium beads was added (mean bead diameter 1 mm; Biospec Products, Inc., Bartlesville PO Box 788, Okla. 74005, USA). Next tubes were completely filled (almost overfilled) with 1× Breaking buffer (3×Breaking buffer=Breaking buffer diluted three times with MilliQ™ water) and carefully and tightly capped. Tubes were loaded into a Mini-BeadBeater-8™ machine (Biospec Products, Inc., Bartlesville PO Box 788, Okla. 74005, USA). Bead beating of yeast cell suspension was run 5× for 1 min at each beating with cooling on ice bath (0° C.) for 1 to 2 min in between beatings. Cell debris and beads were subsequently removed by centrifugation in a microtube centrifuge at 10000×G for 2 min. Supernatants were transferred to new 2.2 mL microtubes and centrifuged at 10000×G for 5 min. Enzyme-containing yeast extract supernatants were aliquoted at 10 µL into 2.2 mL microtubes and subsequently stored at −80° C. before use.

TABLE 1

| 1X Breaking buffer | |
|---|---|
| Ingredient | |
| Tris-Acetate | 150 mM |
| Potassium Acetate | 50 mM |
| Glycerol | 20% v/v |
| EDTA | 1 mM |
| DTT | 1 mM |
| Complete protease inhibitor tablet (Roche Inc.) | one tablet to 75 mL$^{-1}$ |
| MilliQ ™ water | to the required volume |

EXAMPLE 2

Capacity of Prepared Yeast Extract to, Together with RT, Detect BrdUMP Through Phosphorylation and Incorporation into Solid Phase Template/Primer Complex In this experiment a Basic Reaction Mixture in buffer containing reagents listed in Table 2 was used.

TABLE 2

| Basic Reaction Mixture and buffer for the BrdUMP assay. | |
|---|---|
| Ingredient | Final konc. |
| Bis-Tris Propan buffer pH 7.5 | 20.4 mM |
| Oligonucleotide primer (odT) | 0.08 µg/ml |
| Spermidine | 0.1 mM |
| Spermine | 0.1 mM |
| ATP | 0.5 mM |
| $MgCl_2$ | 10.0 mM |
| EGTA | 0.25 mM |
| Triton X-100 | 0.85% v/v |
| DTT | 7.8 mM |
| SIV RT | 10 ng mL$^{-1}$ |
| MilliQ ™ water | to the required volume |

The Basic Reaction Mixture in a buffer was prepared from stock solutions from each component whereupon 100 µL was added to each well of a 96-well plate holding immobilized poly-rA (three plates were set).

Yeast extracts were thawed at 22-25° C. and then put on an ice-bath prior to use. The extract was serially diluted in 5-fold steps and 25 µL of the top concentration was added to the A row while the next to the B row etc. BrdUMP was serially diluted in 10-fold starting at $1.3 \times 10^{-5}$ M and ending at $1.3 \times 10^{-11}$ M. The top concentration corresponded to a concentration 250× less than in the example 1 described preparation. The highest concentration was added to the wells in column 1 of the 96-well plates and the next concentration to column 2 etc. Also a column without BrdUMP was included in each plate, which thereafter was covered and sealed with plastic adhesive tape (Fasson S695, cat. no. SH 236269, Nunc Denmark). Then all three plates were incubated at 33° C. The 1$^{st}$ plate was washed after 3 h of incubation and then put at −20° C. The 2$^{nd}$ plate was washed after 24 h and put at −20° C. and the 3$^{rd}$ plate was washed after 48 h of incubation and put at −20° C. The plates were removed from −20° C. and washed by four consecutive submersions into 4×1 L of Wash-Buffer pH 8.6 (3 mM Tris-HCl, 0.01% Tween-20, 0.5% Triton X-100, 0.25% EtOH CavidiTech AB, Uppsala Sweden). In order to visualize incorporated BrdUMP into the solid-face, 100 ml of a tracer (AP, i.e. alkaline phosphatase conjugated to an anti-BrdUMP monoclonal antibody, RT product Tracer HS, CavidiTech AB, Uppsala, Sweden) was added to each well and incubated for 90 min at 33° C. The plates were again washed by four consecutive submersions into 4×1 L of Wash-Buffer pH 8.6 (3 mM Tris-HCl, 0.01% Tween-20, 0.5% Triton X-100, 0.25% EtOH CavidiTech AB, Uppsala Sweden). After washing 125 microliter of a solution containing pNPP substrate 0.5 mgmL$^{-1}$, 1 mM MgCl$_2$ in 200 mM of Tris-HCL pH 9.8, was added to each well. The plates were incubated at room temperature. The Absorbance at OD$_{405}$ was registered with a Syva Micro Trak® EIA reader using filter with a dual wavelength set to w1=405 and w2=630 nm after 5 min and after different intervals for up to 24 h.

The absorbance after 5 min reading was subtracted from each absorbance's at any later reading time point for each well. The absorbance's present was then plotted against the amount of yeast extract used and against BrdUMP concentration. From FIG. 3 it can be seen that the signal increased the more yeast that was used. BrdUMP concentrations down to $1.3 \times 10^{-11}$ M, were detected, see FIG. 3.

EXAMPLE 4

Capacity of the Presented BrdUMP Detection System to Measure s-TK Activity and its Correlation to Radioactive TK Assay For this experiment 20 different sera ranging from normal serum TK activity (e.g. <5 U) up to very high TK activity (>800 U) according to the Prolifigen® TK-REA (Cat#324250/50 tablets, Diasorin S.p.A, Saluggia, Italy) were selected. The Basic Reaction Mixture in a buffer was prepared according to Table 2, however, in addition BrdU giving a final concentration of $2.5 \times 10^{-5}$ M and yeast extract were added to a concentration 12× lower than the highest concentration given in Example 2. 125 µL of this Basic Reaction Mixture in a buffer was added to each well of a 96-well plate holding immobilized poly-rA.

Sera were serially diluted in 5-fold steps starting at 1:5 and ending at 1:625 in Basic Reaction Mixture in a buffer. 25 µL of each serum dilution was added to a well in the microtiter plate holding the Basic Reaction Mixture in a buffer, i.e. a volume corresponding to; 5, 1, 0.2, 0.04 µL of each patient serum was analyzed.

The plate was next sealed with plastic adhesive tape (Fasson S695, cat. no. SH 236269, Nunc Denmark) and incubated for 2 d at 33° C. The plate was washed by four consecutive submersions into 4×1 L of Wash-Buffer pH 8.6 (3 mM Tris-HCl, 0.01% Tween-20, 0.5% Triton X-100 and 0.25% EtOH, CavidiTech AB, Uppsala Sweden). In order to visualize incorporated BrdUMP into the solid-face 100 µL of a tracer (AP, i.e. alkaline phosphatase conjugated to an anti-BrdUMP monoclonal antibody, RT product Tracer HS, CavidiTech AB, Uppsala, Sweden) was added to each well and the plate was then incubated for 90 min at 33° C. The plate was washed by another four consecutive submersions into 4×1 L of Wash-Buffer pH 8.6 (3 mM Tris-HCl, 0.01% Tween-20, 0.5% Triton X-100 and 0.25% EtOH, CavidiTech AB, Uppsala Sweden). After washing 125 µL of a solution containing pNPP substrate 0.5 mgmL$^{-1}$ in 1 mM of MgCl$_2$, 200 mM of Tris-HCL, pH 9.8 was added to each well. The plate was incubated at room temperature. The Absorbance at OD$_{405}$ was registered with a Syva Micro Trak® EIA reader using filter with a dual wavelength set to w1=405 and w2=630 nm already 5 min after adding the pNPP substrate and thereafter at different intervals for up to 24 h.

The absorbances at 5 min reading were subtracted from each absorbance's at any later reading time point for each well. The $A_{405}$ values were recalculated to $A_{405}$ per h using readings within the reading range of the ELISA reader. The results for the patient sera using 1 µL and 5 µL, respectively, are illustrated in FIG. 4 where the absorbances are related to the TK activity present in the sera according to the existing radioactive Prolifigen® TK-REA (Cat# 324250/50 tablets, Diasorin S.p.A, Saluggia, Italy). The results show a strong correlation between the assay according to the invention and the existing radioactive Prolifigene® TK-REA.

References.

1. Arnér, Elias S. J. and Eriksson Staffan. Mammalian Deoxyribonucleoside Kinases. Pharmac. Ther. 67(2): 155-186. 1995.
2. Gronowitz J. S., Källander C. F. R. TK-REA patent. A method for determining dTK isoenzyme activity and use thereof. EP 94923. Pr. May 14, 1982 SE82030401. EP filing date Oct. 5, 1983.
3. Gronowitz J. S., Källander C. F. R., Diderholm H., Hagberg H. and U. Petterson. Application of an in vitro assay for serum thymidine kinase: results on viral disease and malignancies in humans. Int. J. Cancer, 33:5-12, 1984.
4. Gronowitz J. S., Källander C. F. R, Hagberg H. and L. Persson. Deoxythymidine kinase in cerebrospinal fluid: A potential "marker" for brain tumors. Acta Neurochir. 73:1-12, 1984.
5. Doi S, Naito K, Yamada K. Serum deoxythymidine kinase as a progressive marker of heatological malignancy. Nagoya J Med Sci. 1990 March; 52(1-4):19-26.
6. Eriksson B., Hagberg H., Glimelius B., Sundström C., Gronowitz J. S. and Källander C. F. R. Serum thymidine kinase as a prognostic marker in Hodgkin's disease. Acta Radiol. Oncol. 24:167-71, 1985.
7. Hagberg H., Gronowitz J. S., Killander A., Källander C. F., Simonsson B., Sundström C. and G. Öberg. Serum thymidine kinase in acute leukemia. Brit. J. Cancer 49:537-540, 1984.
8. Morgan M. A. M., Cooper E. H., Bailey C. C., Gronowitz J. S. and C. F. R. Källander. Serum deoxythymidine kinase in acute lymphoblastic leukaemia in children. Tumour Diagnostik & Therapie 6:155-158, 1985.
9. Rehn S., Gronowitz J. S., Källander C., Sundström C., and B. Glimelius. Deoxythymidine kinase in tumour cells and serum of patients with non-Hodgkin lymphomas. Brit. J. Cancer 71:1099-1105, 1995.
10. Simonsson B., Källander C. F. R., Brenning G., Killander A. and J. S. Gronowitz. Evaluation of serum deoxythymidine kinase as a marker in multiple myeloma. Brit. J. Haematol. 61:215-224, 1985.
11. Letocha H., Eklöv S., Gronowitz J. S., Norle'n B-J., and S. Nilsson. Deoxythymidine kinase in the staging of prostatic adenocarcinoma. The Prostate, 29:15-19, 1996.
12. Gronowitz J. S., Bergström R., Nou E. Påhlman S., Brodin O., Nilsson S., and C. F. R. Källander. Clinical and serological markers of stage and prognosis of small cell lung cancer (SCCL): A multivariate analysis. Cancer, 66:722-32, 1990.
13. Zhang F, Li H, Pendleton A R, Robison J G, Monson K O, Murray B K, O'Neill K L Thymidine kinase 1 immunoassay: a potential marker for breast cancer. Cancer Detect Prev. 2001;25(1):8-15.
14. Seah L H, Ton S H, Cheong S K, Hamidah N H. An in-house assay for serum deoxythymidine kinase. Malays J Pathol. December 1991;13(2):109-13
15. Ohrvik A, Lindh M, Einarsson R, Grassi J, Eriksson S. Sensitive nonradiometric method for determining thymidine kinase 1 activity. Clin Chem. 2004 September; 50(9):1597-606. Epub 9 Jul. 2004.
16. Armstrong B. The development of a TK tumor maker system for cancer diagnosis, staging and treatment monitoring. Theses submitted for the degree of doctor of philosophy, University of Ulster., 1991
17. Chaperon. D. New recombinant host cell line comprising a thymidylate kinase gene and/or thymidylate synthase gene that have been functionally complemented by at lest one functional homologue of an other organism, useful in activity testing. WO 200411627 Pr. 7 Jul. 2002 US2002398948. PCT filing date 24 Jul. 2003.
18. Ekstrand D. H. L., Awad R., Källander Clas F. R and J. Simon Gronowitz. A Sensitive Assay For Quantification of RT Activity, based on the use of Carrier Bound Template and Non Radioactive Product Detection, with Special Reference to HIV Isolation. Biotechn. Appl. Biochem. (1996) 23, 95-105.

The invention claimed is:

1. A method for determination of thymidine kinase (TK) activity in a biological sample comprising the steps of:
   contacting, in a container containing a single stranded polynucleotide as a primer or template attached to a solid surface, a Basic Reaction Mixture, in a buffer, comprising the following components: a single stranded polynucleotide as a template and/or primer not attached to a substrate, a modified deoxy nucleoside as a kinase enzyme substrate, a phosphate donor, a nucleotide polymerizing enzyme, and a kinase enzyme source devoid of TK activity, with the biological sample,
   incubating the mixture,
   optionally washing the incubated mixture to remove non-attached reaction components,
   adding to the incubated mixture a labeled affinity molecule with affinity for the modified deoxy nucleoside;
   determining the amount of modified deoxy nucleoside that has been incorporated into the solid surface-attached primer or template by determining the amount of attached labelled affinity molecule, and
   determining the TK activity present in the biological sample from the amount of incorporated modified deoxy nucleoside.

2. The method according to claim 1, wherein the incubated mixture is washed and wherein the determination of the amount of incorporated modified deoxy nucleoside is made by adding to the incubated mixture a labeled affinity molecule with affinity for the modified deoxy nucleoside and determining the amount of modified deoxy nucleoside that has been incorporated by determining the amount of attached labeled affinity molecule with the aid of the label.

3. The method according to claim 1, wherein the kinase enzyme source is selected from the group consisting of a mammalian cell line extract devoid of TK activity, a fungal cell line extract devoid of TK activity, a bacterial cell line extract devoid of TK activity, a combination of thymidylate kinase (TMPK) and Nucleoside di-phosphate kinases (NdK) from purified mammalian cell extracts, a combination of TMPK and NdK from purified fungal cell extracts, a combination of TMPK and NdK from purified bacterial cell extracts, a combination of recombinant mammalian TMPK and recombinant mammalian NdK, a combination of recombinant fungal TMPK and recombinant fungal NdK, and a combination of recombinant bacterial TMPK, recombinant bacterial NdK, and any combinations of TMPK and NdK from the mentioned sources.

4. The method according to claim 3, wherein the kinase enzyme source is a yeast cell extract.

5. The method according to claim 4, wherein the yeast of the yeast cell extract is *Saccharomyces cerevisiae*.

6. The method according to claim 1, wherein the modified deoxy nucleoside is selected from the group consisting of BromodeoxyUridine, Iododeoxyuridine, FluorodeoxyUridine and VinyldexoyThymidine.

7. The method according to claim 6, wherein the modified deoxy nucleoside is BromodeoxyUridine.

8. The method according to claim 1, wherein the solid surface is a plastic surface.

9. The method according to claim 8, wherein the plastic surface is a plastic microtiter plate.

10. The method according to claim 1, wherein the solid surface-attached single stranded polynucleotide is attached via its 5'-end or immobilized using imidazole in activated plates.

11. The method according to claim 1, wherein the biological sample is selected from the group consisting of blood, serum, plasma, Cerebral Spinal Fluid (CSF), pleural fluid, ascites, tissues, cells and extracts thereof.

12. A method for determination of thymidine kinase (TK) activity in a biological sample, comprising:
   (a) contacting, in a container:
      (I) a single stranded polynucleotide as a primer or template attached to a solid surface;
      (II) a Basic Reaction Mixture, in a buffer, comprising:
         a non-attached single stranded polynucleotide as a template and/or primer,
         a modified deoxy nucleoside as a kinase enzyme substrate,
         a phosphate donor,
         a nucleotide polymerizing enzyme, and
         a kinase enzyme source devoid of TK activity; and
      (III) the biological sample;
   (b) incubating the mixture so that the following occurs:
      (i) the primer and the template polynucleotides hybridize forming a primer extendable complex attached to the solid surface;
      (ii) any TK activity present in the biological sample phosphorylates the modified deoxy nucleotide;
      (iii) the enzymatic activity in the kinase enzyme source devoid of TK activity further converts the phophorylated modified deoxy nucleotide into a nucleotide polymerizing enzyme substrate; and
      (iv) the nucleotide polymerizing enzyme substrate is incorporated into the primer extendable complex by a primer extension reaction catalyzed by the nucleotide polymerizing enzyme;
   (c) optionally washing the incubated mixture to remove components not attached to the solid surface;
   (d) determining the amount of modified deoxy nucleoside that has been incorporated into the solid surface-attached primer or template; and
   (e) determining the TK activity present in the biological sample from the amount of incorporated modified deoxy nucleoside, and wherein the amount of incorporated modified deoxy nucleotide is proportional to the TK activity present in the biological sample.

13. The method according to claim 12, wherein the incubated mixture is washed.

14. The method according to claim 12, wherein the kinase enzyme source is selected from the group consisting of a mammalian cell line extract devoid of TK activity, a fungal cell line extract devoid of TK activity, a bacterial cell line extract devoid of TK activity, a combination of thymidylate kinase (TMPK) and Nucleoside di-phosphate kinases (NdK) from purified mammalian cell extracts, a combination of TMPK and NdK from purified fungal cell extracts, a combination of TMPK and NdK from purified bacterial cell extracts, a combination of recombinant mammalian TMPK and recombinant mammalian NdK, a combination of recombinant fungal TMPK and recombinant fungal NdK, and a combination of recombinant bacterial TMPK, recombinant bacterial NdK, and any combinations of TMPK and NdK from the mentioned sources.

15. The method according to claim 14, wherein the kinase enzyme source is a yeast cell extract.

16. The method according to claim 12, wherein the modified deoxy nucleoside is selected from the group consisting of BromodeoxyUridine, Iododeoxyuridine, FluorodeoxyUridine and VinyldexoyThymidine.

17. The method according to claim 16, wherein the modified deoxy nucleoside is BromodeoxyUridine.

18. The method according to claim 12, wherein the solid surface is a plastic surface.

19. The method according to claim 18, wherein the plastic surface is a plastic microtiter plate.

20. The method according to claim 12, wherein the solid surface-attached single stranded polynucleotide is attached via its 5'-end or immobilized using imidazole in activated plates.

21. A method for determination of thymidine kinase (TK) activity in a biological sample selected from the group consisting of blood, serum, plasma, Cerebral Spinal Fluid (CSF), pleural fluid, ascites, tissues, cells and extracts thereof, comprising:
(a) contacting the biological sample with a single stranded polynucleotide attached via the 5'-end or immobilized using imidazole to a solid surface and a Basic Reaction Mixture in a buffer, wherein said Basic Reaction Mixture comprises, in a container:
    (I) a single stranded polynucleotide not attached to a solid surface,
    (II) a modified deoxy nucleoside as a kinase enzyme substrate, wherein said modified deoxy nucleoside is selected from the group consisting of BromodeoxyUridine, Iododeoxyuridine, FluorodeoxyUridine and VinyldexoyThymidine,
    (III) a phosphate donor,
    (IV) a nucleotide polymerizing enzyme, and
    (V) a kinase enzyme source devoid of TK activity;
(b) incubating the mixture so that the following occurs:
    (i) the single stranded polynucleotide attached to a solid surface and the single stranded polynucleotide not attached to a solid surface hybridize to form a primer extendable complex attached to the solid surface;
    (ii) any TK activity present in the biological sample phosphorylates the modified deoxy nucleotide;
    (iii) the enzymatic activity in the kinase enzyme source devoid of TK activity further converts the phophorylated modified deoxy nucleotide into a nucleotide polymerizing enzyme substrate; and
    (iv) the nucleotide polymerizing enzyme substrate is incorporated into the primer extendable complex by a primer extension reaction catalyzed by the nucleotide polymerizing enzyme;
(c) washing the incubated mixture to remove components not attached to the solid surface;
(d) determining the amount of modified deoxy nucleoside that has been incorporated into the primer extendable complex; and
(e) determining the TK activity present in the biological sample based on the amount of modified deoxy nucleoside that has been incorporated into the primer extendable complex.

22. The method according to claim 1, wherein said labeled affinity molecule is an enzyme-antibody conjugate, where the antibody of said enzyme-antibody conjugate has affinity for the modified deoxy nucleoside.

* * * * *